US009722480B2

(12) United States Patent
Kelp (10) Patent No.: US 9,722,480 B2
(45) Date of Patent: Aug. 1, 2017

(54) POSITION CONTROLLED ELECTRODYNAMIC LINEAR MOTOR (71) Applicant: Karl Storz GmbH & Co. KG, Tuttlingen (DE)

(72) Inventor: Martin Kelp, Berlin (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 241 days.

(21) Appl. No.: 14/720,779

(22) Filed: May 23, 2015

(65) Prior Publication Data

US 2015/0340939 A1 Nov. 26, 2015

(30) Foreign Application Priority Data

May 23, 2014 (DE) .......................... 10 2014 107 297

(51) Int. Cl.
*H02K 41/035* (2006.01)
*H01F 7/16* (2006.01)
*H02K 33/16* (2006.01)
*H01F 7/122* (2006.01)
*H02K 33/12* (2006.01)
*H02K 11/215* (2016.01)

(52) U.S. Cl.
CPC .......... *H02K 41/035* (2013.01); *H01F 7/122* (2013.01); *H01F 7/1615* (2013.01); *H02K 11/215* (2016.01); *H02K 33/12* (2013.01); *H02K 33/16* (2013.01); *H02K 41/0356* (2013.01)

(58) Field of Classification Search
CPC ...... H02K 11/215; H02K 33/12; H02K 33/14; H02K 33/16; H02K 41/035; H02K 41/0356; H01F 7/122; H01F 7/1615; G02B 7/04–7/1805
See application file for complete search history.

(56) References Cited

U.S. PATENT DOCUMENTS

| 5,478,650 A | 12/1995 | Davanloo et al. |
| 5,747,952 A | 5/1998 | Izawa et al. |
| 5,748,650 A | 5/1998 | Blaker et al. |
| 7,365,768 B1 | 4/2008 | Ono et al. |

(Continued)

FOREIGN PATENT DOCUMENTS

| DE | 2946147 A1 | 5/1980 |
| DE | 4012832 A1 | 10/1991 |

(Continued)

*Primary Examiner* — Ramon M Barrera
(74) *Attorney, Agent, or Firm* — Whitmyer IP Group LLC (57) ABSTRACT A linear drive for a miniaturized optical system, as used for example in an endoscope, includes a stator and an armature. The stator has a coil with two stator pole shoes arranged in axial direction, and two magnetic field sensors arranged at the outer side of the stator pole shoes. The armature has permanent magnets which are polarized in opposite directions, and a center armature pole shoe between the two permanent magnets, and an armature pole shoe at each side of the permanent magnet, opposite to the center armature pole shoe in axial direction. The magnetic field of the outer armature pole shoe goes completely or only in part, dependent from the armature position, through the magnetic field sensor and thus generates a position-dependent signal. This signal can be used for measuring and/or controlling the position of the armature.

25 Claims, 5 Drawing Sheets

(56) References Cited

U.S. PATENT DOCUMENTS

| | | | |
|---|---|---|---|
| 8,278,785 B2* | 10/2012 | Schrader | H02K 41/0352 310/12.16 |
| 2004/0021458 A1 | 2/2004 | Imamura | |
| 2008/0310037 A1 | 12/2008 | Kuo et al. | |
| 2011/0170288 A1 | 7/2011 | Kim | |
| 2012/0098469 A1 | 4/2012 | Takeuchi | |

FOREIGN PATENT DOCUMENTS

| | | |
|---|---|---|
| DE | 19605413 A1 | 7/1996 |
| DE | 10323629 A1 | 10/2004 |
| DE | 102006040779 A1 | 6/2007 |
| DE | 102008038926 A1 | 2/2009 |
| DE | 102010000582 A1 | 9/2011 |
| GB | 2243488 A | 10/1991 |
| JP | 2000092809 A | 3/2000 |

\* cited by examiner

Fig. 11 ially symmetrical. Thereby, the components are largely formed ring-shaped. The movement of the armature is performed along an axis, which is preferably parallel to the center axis of the rotationally symmetrical arrangement, and which is most preferably on the center axis. The stator has one or two coils, wherein at least one stator pole shoe is arranged preferably in axial direction, laterally to the coils, as well as a magnetic member is arranged in radial direction at the outside. This magnetic member is at least largely parallel to the movement direction, and preferably encloses said one or two coils, and more preferably encloses at least one stator pole shoe. Preferably, the magnetic member comprises a soft magnetic material and most preferably a material comprising iron or ferrite. The armature is at least partially enclosed by the coil in radial direction, and has a first permanent magnet and optionally a second permanent magnet. Preferably, an armature pole shoe, respectively, is arranged laterally in axial direction at each of the permanent magnets. In the case of two permanent magnets, one further pole shoe is arranged between the two permanent magnets. The armature pole shoes allow a defined flow of the magnetic fields of the permanent magnets through the coil towards the magnetic member. Basically, the arrangement also may work without pole shoes. However, by means of the pole shoes, the force of the motor can be increased by more than one magnitude. In the case of two permanent magnets, these are magnetized axially and are aligned in their polarization such that either the north poles or the south poles are located opposite to one another. The armature and in particular the permanent magnets as well as the pole shoes are preferably hollow-cylindrical, that is they have the form of a cylindrical sleeve. The beam path of an optical system can then go through the sleeve. In particular, a lens or another optical element can be positioned in the sleeve. Consequently, the focal length
POSITION CONTROLLED ELECTRODYNAMIC LINEAR MOTOR

CROSS-REFERENCE TO RELATED APPLICATIONS

This application claims priority to pending German Application No. 102014107297.9 filed on May 23, 2014.

FIELD OF THE INVENTION

The invention relates to a linear motor also called linear drive, in particular for optical systems. Such optical systems are used for example in endoscopes. In modern video endoscopes, a camera chip together with a lens system are integrated in the endoscope tip. A miniaturized motor is required to adjust the focal length and the focus point of the lens system.

BACKGROUND OF THE INVENTION

Endoscopes as known from prior art, for example, for minimally invasive surgery, guide an image by means of rod lenses from an intracorporeal objective lens to an extracorporeal occular. Due to the rod lenses, the system is rigid and limited in optical quality. Modern video endoscopes use a camera chip in the endoscope tip. Such an endoscope is disclosed in U.S. Pat. No. 7,365,768 B1. This has a rigidly arranged lens in front of the camera chip. An adjustment of the focal length of the lens is not possible.

DE 103 23 629 A1 discloses a moving field linear motor which includes at least three stator coils. A phase-shifted current supply to the coils produces a moving field which effects a displacement of the armature with axial permanent magnets.

From DE 10 2008 038 926 A1, a linear drive including two axially polarized permanent magnets in an armature is known. The armature is deflected in axial direction by the current supply to the stator coils. Additionally, stable positions of the armature are realized by pole shoes mounted to the stator, allowing a continuous displacement of the armature in a guiding tube.

In DE 10 2010 000 582 A1, a further linear drive is disclosed, which has an axially polarized permanent magnet in the armature, and one or two axially polarized permanent magnets in the stator.

These three linear drives each include a stator and an armature. The armatures are construed of one or several permanent magnets. For deflection and for generation of the electromagnetic flux in defined directions, rings of soft magnetic iron are disposed at the permanent magnets (pole shoes). One or more coils generate Lorentz-forces in the stator. Additional permanent magnets and rings of soft magnetic iron serve partially for generation of reluctance forces. The stator is enclosed by a soft-magnetic sleeve which constitutes a reflux yoke for the magnetic flux. In a current less state, the armature is in a so-called idle position due to resetting reluctance forces. Due to supplying the coils with electric current of constant current strength, Lorentz-forces are generated which lead to a continuous deflection of the armature from the rest position. By generating a force balance of Lorentz-forces in the DE 103 23 629 A1, or of Lorentz-forces and reluctance forces in DE 10 2008 038 926 A1 and DE 10 2010 000 582 A1, the armature stays in a deflected position. Thereby it is preferred to have a predetermined relationship between the magnitudes of currents to positions of the armature. Normally, this in achieved by calibration after setup of the drives.

External forces which are difficult to control, such as for example friction forces or gravity, lead to positioning inaccuracy. By predefining fixed magnitudes of current, the position of the armature can be determined only in a limited manner.

DE 196 05 413 A1 discloses a linear drive with position measurement. Here, the drive winding is at the same time used as measurement winding. By such a position measurement, a higher positioning accuracy can be achieved. However, the preciseness of the measurement system and thus of the control system is limited due to the minor change of the coil inductivity during movement of the armature.

In U.S. Pat. No. 5,747,952, a three-phase linear drive is disclosed, where the magnetic field is measured by a Hall sensor between coil and armature, and the amplitude of the control signal is held at a constant value.

SUMMARY OF THE INVENTION

The embodiments are based on the object of improving a linear drive such that the armature can be brought in defined positions, and a defined and preferably linear characteristic curve exists between the control signal and the armature's position. Furthermore, the position of the armature should preferably be independent to a large extent from an external load. The linear drive should be miniaturizable to such an extent that it may be inserted into an endoscope.

In an embodiment, a linear drive comprises a stator and an armature which is linearly displaceable thereto. Preferably, the linear drive is built mainly rotationally symmetrical. Thereby, the components are largely formed ring-shaped. The movement of the armature is performed along an axis, which is preferably parallel to the center axis of the rotationally symmetrical arrangement, and which is most preferably on the center axis. The stator has one or two coils, wherein at least one stator pole shoe is arranged preferably in axial direction, laterally to the coils, as well as a magnetic member is arranged in radial direction at the outside. This magnetic member is at least largely parallel to the movement direction, and preferably encloses said one or two coils, and more preferably encloses at least one stator pole shoe. Preferably, the magnetic member comprises a soft magnetic material and most preferably a material comprising iron or ferrite. The armature is at least partially enclosed by the coil in radial direction, and has a first permanent magnet and optionally a second permanent magnet. Preferably, an armature pole shoe, respectively, is arranged laterally in axial direction at each of the permanent magnets. In the case of two permanent magnets, one further pole shoe is arranged between the two permanent magnets. The armature pole shoes allow a defined flow of the magnetic fields of the permanent magnets through the coil towards the magnetic member. Basically, the arrangement also may work without pole shoes. However, by means of the pole shoes, the force of the motor can be increased by more than one magnitude. In the case of two permanent magnets, these are magnetized axially and are aligned in their polarization such that either the north poles or the south poles are located opposite to one another. The armature and in particular the permanent magnets as well as the pole shoes are preferably hollow-cylindrical, that is they have the form of a cylindrical sleeve. The beam path of an optical system can then go through the sleeve. In particular, a lens or another optical element can be positioned in the sleeve. Consequently, the focal length and/or the focus point of the optical system can be adjusted by a displacement of the sleeve.

The pole piece and/or the magnetic member preferably comprise ferromagnetic and/or soft magnetic materials. Most preferably, these materials comprise iron or ferrite.

The linear motor may easily be miniaturized as far as to a size of a few millimeters external diameter.

Preferably, the coils may be wound onto a coil form or without a coil form, as desired. It may also be multi-part, i.e. it may comprise of a plurality of windings.

For indirect determination of the position of the armature, one or two magnetic field sensors, herein also called field sensors, are provided. Basically, also a higher number of field sensors may be provided. The magnetic field sensors are arranged laterally in axial direction next to the at least one winding. A part of the magnetic flux through the permanent magnets is, dependent from the position of the armature, through these magnetic field sensors. By determining the magnetic flux and the corresponding magnetic flux density B, the position of the armature can be concluded. Due to a one-phase current supply of the coils, the control electronics can be easily realized. The simple construction allows for miniaturization of the drive, such that it is suitable for use in minimal-invasive instruments.

Preferably, the at least one magnetic field sensor is arranged laterally next to at least one stator pole shoe. Alternatively, at least one magnetic field sensor can also be integrated in a stator pole shoe. The evaluation of the signal difference of at least two magnetic field sensors is particularly advantageous. Thereby, improved independence of external influences, such as temperature, as well as higher measurement accuracy may be achieved.

In a preferred embodiment a coil and on both sides of the coil in axial direction stator pole shoes are provided, wherein the coil and the stator pole shoes are enclosed by a magnetic member. Two magnetic field sensors are provided laterally next to the stator pole shoes, or are integrated into the stator pole shoes, respectively. The armature has two permanent magnets which are polarized in opposite directions, and preferably magnetized axially, wherein between these two permanent magnets, an armature pole shoe is provided, and at the ends of the permanent magnets two further armature pole shoes are provided. A further embodiment of the linear drive has only one stator pole shoe and only one field sensor. The armature may be simply comprise only one permanent magnet and preferably has two armature pole shoes at the ends of the permanent magnet.

In a further embodiment, two coils are arranged laterally in axial direction at two sides of a stator pole shoe. Here, at least one magnetic field sensor, preferably two magnetic field sensors are integrated in the stator pole shoe. Preferably, here an armature with two oppositely polarized permanent magnets and one armature pole shoe between the permanent magnets as well as at the outer ends of the permanent magnets is provided.

For measuring the magnetic field, various sensor types may be used. The most common sensors are Hall effect sensors, GMR sensors, and AMR sensors.

For the linear drive no balance state between reluctance force and Lorentz-force is required for the positioning, as it is necessary for the linear drives known from the prior art. This results in comparatively significantly higher drive and actuating forces at equal electrical power. Therefore, it can also be used in surgical instruments.

Further embodiments of the linear drive may also be realized with an ironless stator. Here, the stator pole shoes and the magnetic member would consist of non-ferromagnetic material or would even be omitted. Due to the absent magnetic field conductive materials in the stator, the magnetic flux density in the magnetic circuit is reduced. Thereby, also the driving Lorentz-force by an electrical current flow in the coil is reduced.

In a further advantageous embodiment, there is a sliding layer between the stator and the armature. This sliding layer can be implemented as a sliding sleeve, in particular in the case of a rotationally symmetric arrangement. In order to influence the magnetic fields as little as possible, the sliding layer preferably comprises of non-magnetic-field-conductive material, particularly a non-ferromagnetic material. Its surface preferably comprises a material with low friction coefficient, for example PTFE (polytetrafluoroethylene), silicon nitride, silicon carbide, poly-para-xylylene polymers, or DLC (diamond like carbon), like for example disclosed in U.S. Pat. No. 5,478,650.

The sliding layer may compensate for unevenness on the side of the stator facing the armature.

In an alternate embodiment, the linear drive can be realized with a flat stator, e.g. having a plate-shaped structure and likewise flat or plate-shaped pole piece of the armature. Alternatively, a plurality of linear drives disposed around a cylinder or a polygonal body may also be provided. A stable guidance is obtained, for example, in the case of a uniform arrangement of linear motors around a cylinder.

In another embodiment, the linear drive can also consist of solid material and have a plunger at one end for the nano-positioning of instruments. Such a device can preferably be used in molecular biology, microelectronics or neurosurgery.

Due to the simple arrangement, the linear drive may be realized very compact with respect to axial building length. Therefore, the linear drive is well-suited for an embodiment with a hollow armature in optical systems.

The linear drive may be integrated directly into the objective lens of an endoscope camera. The controlled adjustment of zoom and focus functions with measurement of the position of the moveable optical lens groups is therefore possible. Due to the small size, also stereo cameras with two single objectives lenses for 3D systems may be integrated in a space-saving manner into conventional camera housings. The linear drive preferably is integrated twice in identical construction manner for the movement of lens groups along the optical axis. Due to the controlled positioning of the lens groups by the linear drives, the images projected on the image sensors can be displayed clearly.

In chip-on-the-tip-objective lenses, the complete optics, including a camera chip may be integrated into the tip of the endoscope. Thereby, optical lens groups are moved, for example, along the optical axis, in order to allow a focusing or zooming of the image. The controlled linear drive may be used in miniaturized form also in video endoscopes. By the inventive drive, it is possible to control the position of the lens groups by means of feedback of the positioning signals. By measurement of the armature position by means of the magnetic field sensors, the position of the lens groups is known. In a drive for focus adjustment, with knowledge about the optical system, the object distance to focused objects can thereby be determined. With help of the inventive linear drive, also a simple coupling of two or more movable lens groups is possible. In stereo endoscopes in chip-on-the-tip-embodiment, two neighbored optical lens systems at the endoscope tip are often used for the stereo imaging. If here, lens groups should be axially movable for focus or zoom function, respectively, two inventive drives may be used for this purpose.

By use of the drive in a surgical instrument it is possible to control the aperture angle Phi of a jaw section. The armature can be positioned in the stator by means of the magnetic field sensors, as described above. If a pull-push-rod, which initiates opening and closing of the jaw section by linear movement, is mounted in the drive, the aperture angle Phi of the instrument can be adjusted by the position of the armature. By the controlled operation, the aperture angle Phi can be maintained or adjusted, independent of the clamp force of the jaw section. As the inventive motor is a motor driven by Lorentz force, the axially acting drive force can be determined through the relation of current strength in the coil. Thereby, also the clamping force of the jaw section can be calculated. This relationship plays an important role especially in novel force-feedback-systems, in which the operating physician receives feedback about the clamping force of the jaw section.

BRIEF DESCRIPTION OF THE DRAWINGS

In the following, the invention will be described by way of example, without limitation of the general inventive concept, on examples of embodiment and with reference to the drawings.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

Figure 1:
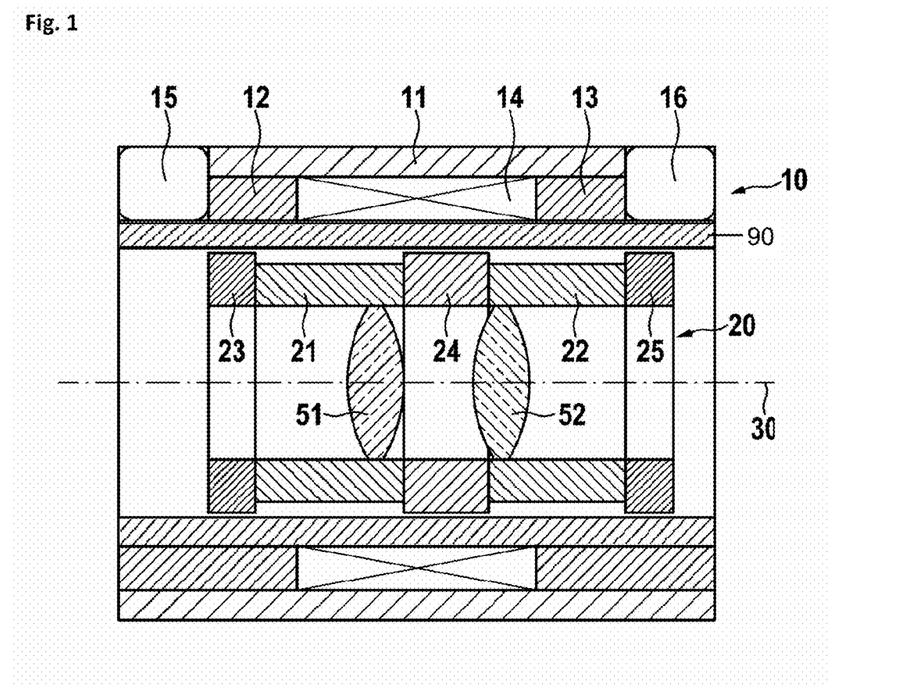
FIG. 1 schematically shows a linear drive in a longitudinal section.

FIG. 1 schematically shows a linear drive in a longitudinal section. According to a preferred embodiment, the linear drive is arranged mainly rotationally symmetric around the center axis 30. It comprises a stator 10 and an armature 20.

The stator 10 has a coil 14, which preferably is enclosed by a cylindrical magnetic member 11 in radial direction. The coil 14 is enclosed by a first stator pole shoe 12 and a second stator pole shoe 13 in axial direction. Preferably, also these stator pole shoes are enclosed by the magnetic member in radial direction. Furthermore, a first magnetic field sensor 15 is arranged at the side of the first stator pole shoe 12 in axial direction next to the coil, and a second magnetic field sensor 16 is arranged at the side of the second stator pole shoe 13 in axial direction next to the coil 14. Preferably, at least one magnetic field sensor is arranged in an opening of a stator pole shoe. More preferably, this opening extends in axial direction, as shown in this Figure, but it may also extend in radial direction. The opening may be continued into the magnetic member 11, in order to offer sufficient mounting space for a bigger field sensor. Preferably, the stator pole shoes and/or the magnetic member are ring-shaped.

The armature has a first permanent magnet 21 and a second permanent magnet 22, which are polarized in opposite directions and preferably parallel to the center axis. A center armature pole shoe 24 is arranged between the two permanent magnets. At the sides opposite to the center armature pole shoe 24 in axial direction, a first outer armature pole shoe 23 is arranged towards the first pole shoe 21, and a second outer armature pole shoe 25 is arranged towards the second pole shoe 22. Preferably, the armature is hollow, more preferably hollow-cylindrical. Preferably, the permanent magnets and/or armature pole shoes are ring-shaped. In some embodiments, a sliding sleeve 90 may be arranged between the stator 10 and the armature 20.

Preferably, the two magnetic field sensors 15, 16 are arranged in the same plane through the center axis 30, but they may also be arranged in other planes.

Preferably, the drive is construed such that within the moving distance, no axially directed reluctance forces act in a currentless state. If the coil 14 is energized, a Lorentz-force is generated, which acts on the armature, independently of its position.

Basically, this embodiment, as well as all other embodiments illustrated in this specification, may be realized with an ironless stator. Thereby, the stator pole shoes 12, 13 as well as the magnetic member 11 would consist of non-ferromagnetic material or would even be omitted. Due to the absent magnetic field conductive materials in the stator, the magnetic flux density in the magnetic circuit is reduced. Thereby, also the driving Lorentz-force by an electrical current flow in the coil is reduced.

Figure 2:
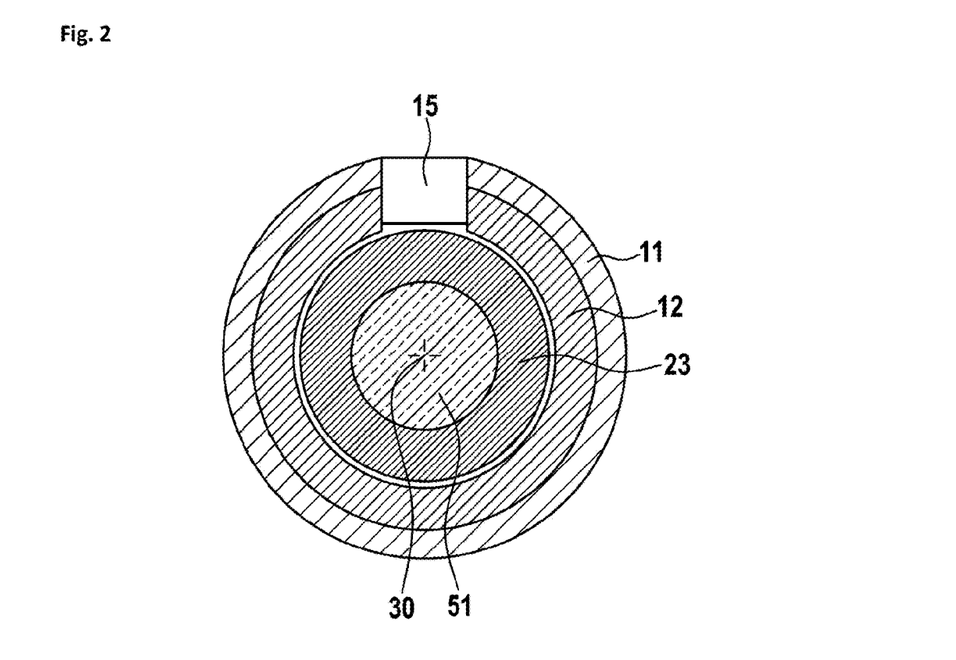
FIG. 2 shows a linear drive in a cross-section.

In FIG. 2, a view towards the center axis 30 is shown. Here, the preferred concentric arrangement of the components is illustrated in detail. In this embodiment, the first field sensor 15 is arranged in an opening, which protrudes through the magnetic member 11 into the first stator pole shoe.

Figure 3:
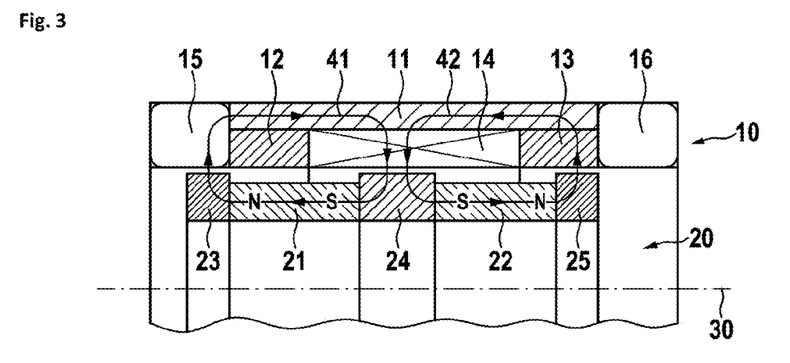
FIG. 3 shows the magnetic flux in a first armature position.
Figure 4:
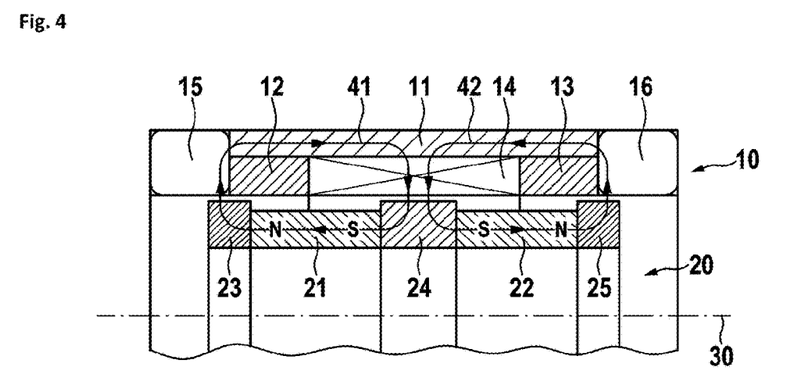
FIG. 4 shows the magnetic flux in a second armature position.
Figure 5:
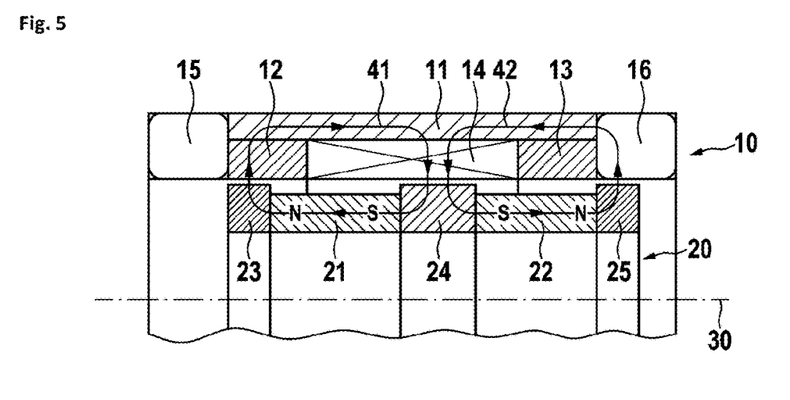
FIG. 5 shows the magnetic flux in a third armature position.

In FIGS. 3, 4 and 5, the magnetic field profiles in different positions of the armature 20 relative to the stator 10 are shown. In FIG. 3, the armature 20 is shown displaced to the left relative to the center position, which is shown in FIG. 4. In FIG. 5, it is displaced to the right. Basically, a first magnetic circuit 41 is generated, starting from the first permanent magnet 21. The magnetic field goes through the first outer armature pole shoe 23 via the first field sensor 15 and the first stator pole shoe 12, respectively, continuing through the magnetic member 11, via the coil 14 and further continuing to the center armature pole shoe 24 and back to the first permanent magnet 21. Accordingly, the second magnetic circuit 42 is oriented in opposite direction.

The lines 41 and 42 symbolically illustrate the magnetic field curve. In fact, the magnetic field spreads, for example, over the whole front side of the permanent magnets 21, 22. Similarly, the magnetic field spreads in radial direction out of the armature pole shoes over the surface.

In FIG. 3 it can be seen that a main part of the magnetic field goes through the first field sensor 15, while the negligible part goes through the first stator pole shoe 12. The magnetic field starting from the second armature pole shoe 25 mainly goes over the second stator pole shoe 13 into the magnetic member 11. Only a minimal and negligible part will run through the second field sensor 16.

In FIG. 4, a part of the magnetic field goes out of the first armature pole shoe 23, via the first field sensor 15, and parallel thereto via the first stator pole shoe 12 into the magnetic member 11. Similar holds true for the magnetic field out of the second armature pole shoe 25. Here, the field divides as well between the second field sensor 16 and the second stator pole shoe 13.

In FIG. 5, the main part of the magnetic field goes out of the first armature pole shoe 23 via the first stator pole shoe 12 into the magnetic member 11, while the main part of the magnetic field out of the second armature pole shoe 25 goes through the second field sensor 16.

Figures 6, 7:
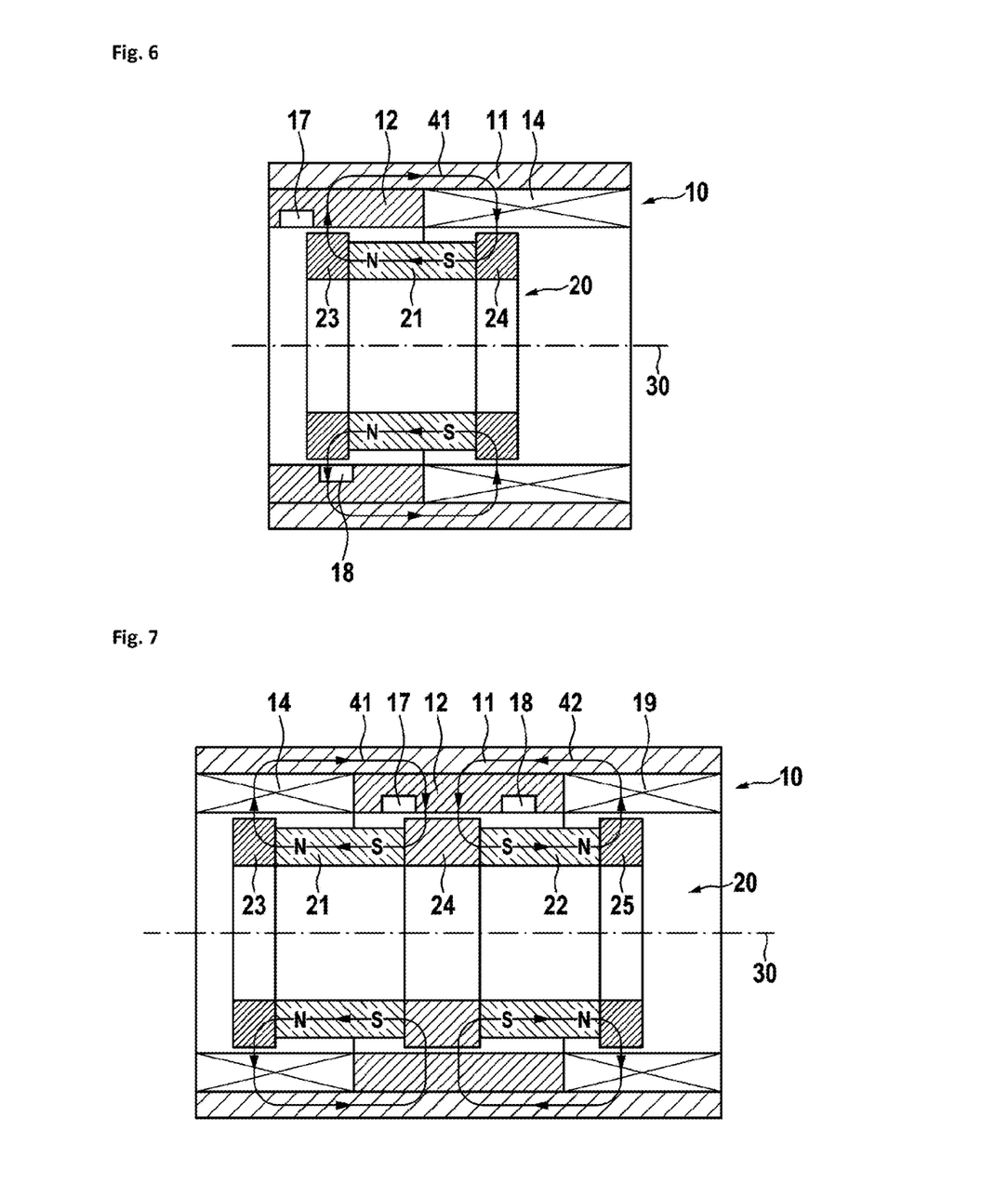
FIG. 6 shows a further embodiment with only one stator pole shoe.
FIG. 7 shows a further embodiment with two coils.

In FIG. 6, a further embodiment is shown. In this embodiment, the stator has only one stator pole shoe 12, and the armature has only one permanent magnet 21. A first field sensor 17 and optionally a second field sensor 18 are provided. Preferably, integrated field sensors 17, 18 with smaller construction size are used, which can be integrated into the first stator pole shoe 12. Preferably, these are inserted into a recess of the first stator pole shoe 12. The field sensors 17, 18 are disposed opposite to each other, in axial direction. Preferably, they can also be arranged in different planes through the rotation axis. In this embodiment, they are arranged in the same plane, on different sides of the rotation axis. Dependent from the position of the armature 20 relative to the stator 10, the magnetic flux flows, starting from the first outer armature pole shoe 23, through one of the field sensors. In the illustrated position, a major part of the magnetic flux flows through the second field sensor 18, while the first field sensor is in a space free of fields.

In the arrangement shown here, the magnetic field sensor can only lie in the magnetic field of a pole shoe. Thereby, simplified magnetic field sensors can be implemented, which deliver an output signal independent of the direction of the magnetic field. Such sensors are, for example, GMR—(Giant Magneto Resistance) sensors. In the prior art, it is often necessary to use direction-sensitive magnetic field sensors, such as Hall sensors, in order to achieve an accurate position determination. Such sensors are in most cases bigger, more expensive, and require a more complex control and evaluation circuitry.

The integration of the magnetic field sensors in the stator pole shoe allows a significantly improved exploitation of space, in particular in miniature motors. This embodiment is at the same time more robust, as the magnetic field sensors are supported mechanically by the stator pole shoe. As a result, a separate housing for the magnetic field sensors can be omitted.

Basically, in this embodiment of a linear drive, also an arrangement with a first magnetic field sensor 15 next to a first stator pole shoe 12, as in the embodiment of FIG. 1, may be implemented. Similarly, the embodiment of FIG. 1 may be realized with a first field sensor 17 which is integrated into the first stator pole shoe 12, according to this embodiment. Preferably, then also the second field sensor 16 of the embodiment of FIG. 1 is replaced by second field sensor 18, which is integrated into the second stator pole shoe 13.

In FIG. 7, a further embodiment of the invention is shown. The armature 20 corresponds to the armature of the first embodiment, as shown, for example, in FIG. 1. Here, the stator has a first coil 14 and a second coil 19. The coils may be operated single-phased (identical current strength) or double-phased (different current strength in both coils). A stator pole shoe 12 is arranged between the two coils. The coils and the stator pole shoe are enclosed by the magnetic member 11. The field sensors 17, 18 are disposed one to another, in axial direction, and are integrated into the stator pole shoe 12, or are received by the recesses of the stator pole shoe. The magnetic field of the middle armature pole shoe 24 goes as a whole or partly—depending on the position of the armature—through the first field sensor 17 or the second field sensor 18. The output signals of the field sensors 17, 18 correspond approximately to the curves 61 and 62 of FIG. 8. Also here, a signal according to FIG. 9 can be achieved by subtraction of the signals.

Figure 8:
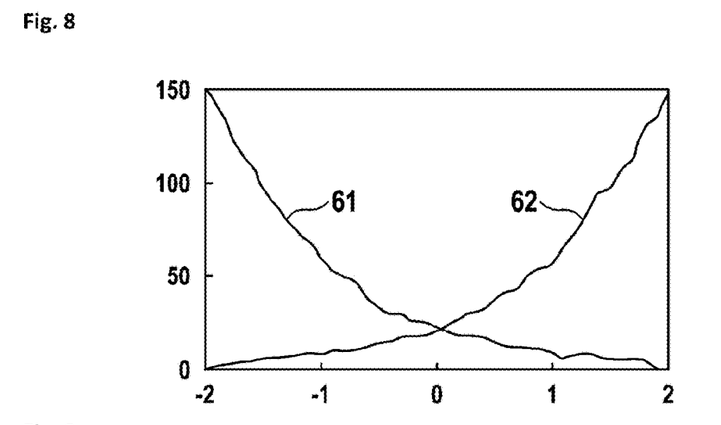
FIG. 8 shows the sensor signals of an embodiment of FIG. 1, in dependence of the position.

FIG. 8 shows the signal curve of the field sensors, for example according to the illustrations in FIGS. 3, 4 and 5. The diagram shows on the horizontal axis the distance relative to the zero position "0" in millimeters, which corresponds, for example, to FIG. 4. A deflection of −2 mm corresponds to FIG. 3, and a deflection of +2 mm corresponds to FIG. 5. On the vertical axis, the amplitudes of the sensor signals are scaled and indicated from 0-150. The curve 61 shows the signal of the first field sensor 15, while the curve 62 shows the signal curve of the second field sensor 16.

Curve 61 shows on the left side, a maximal amplitude at a deflection of −2 mm, which corresponds to the maximal magnetic flux density through the first magnetic field sensor 15. This is achieved by the position of the armature as shown in FIG. 3. At the same time, the second field sensor 16 is in a nearly field free space, such that the sensor signals according to curve 62 are nearly zero. In the center position according to FIG. 4, the flux density of both field sensors is approximately equal, such that also both curves 61 and 62 have the same amplitude at position "0". At the right position at +2 mm, the sensor signals behave in a reversed manner as in the left position. Here, the maximal magnetic flux density is through the first magnetic field sensor 16, while the first field sensor 15 lies in a nearly field free space.

Figure 9:
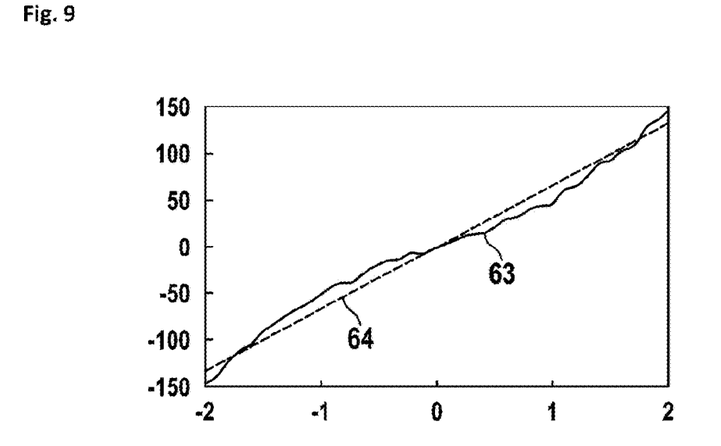
FIG. 9 shows the difference of the sensor signals, in dependence of the position.

FIG. 9 shows the sum of curves 61 and 62 of FIG. 8 in curve 63. This curve can be well approximated by linear approximation 64. A measurement signal results, which is approximately proportional to the position of the armature. This measurement signal generally can be input into a control loop, such that the position of the armature can be kept constant, in dependence of a setpoint value.

Figure 10:
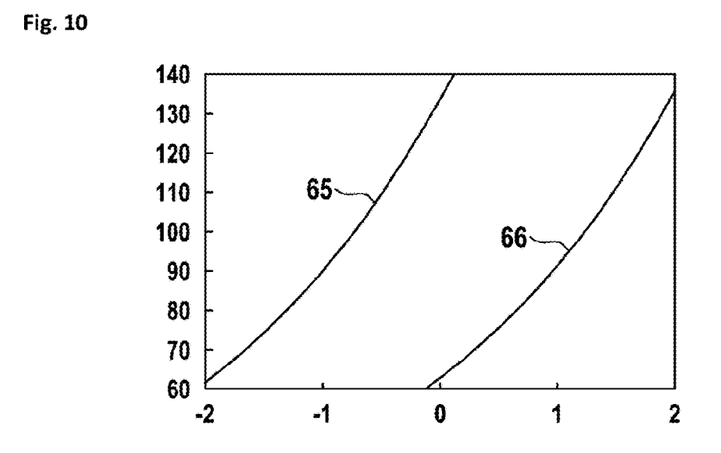
FIG. 10 shows the sensor signals in an embodiment according to FIG. 6.

FIG. 10 shows the signals of the field sensors in an arrangement according to FIG. 6. Also here, the horizontal axis shows the displacement towards the center axis, while the vertical axis indicates the amplitude of the sensor signals. Curve 65 indicates the signal amplitude of the first field sensor 17, while the second curve 65 indicates the signal amplitude of the second field sensor 18. As a result, the exact position can be determined by evaluating which sensor outputs a signal, in combination with the signal amplitude of the sensor. In this example, only two sensors are shown. Of course, any higher number of magnetic field sensors may be used, in order to increase the resolution and/or maximal path length.

Figure 11:
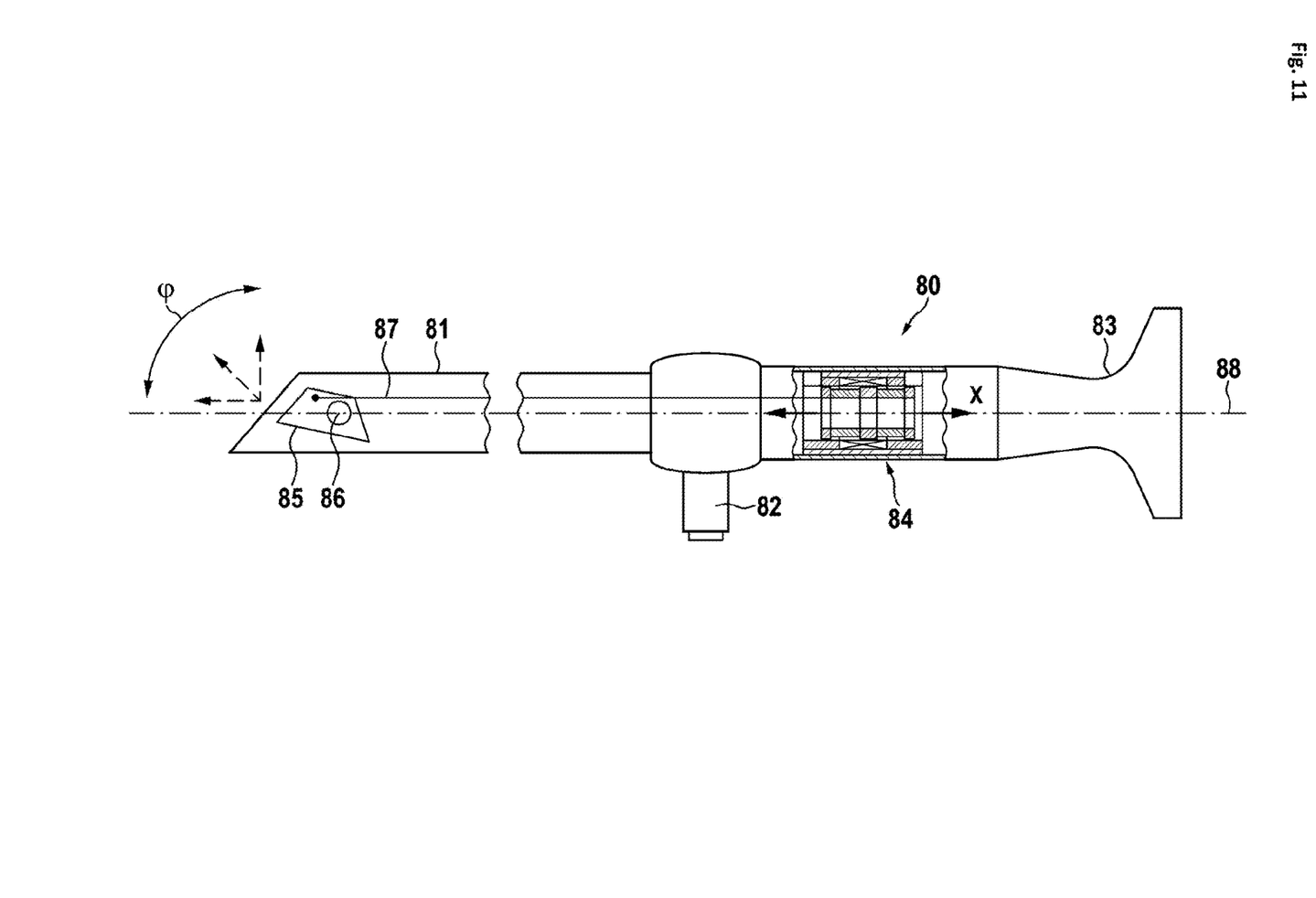
FIG. 11 shows an endoscope with a prism pivotable by a linear motor.

FIG. 11 shows an endoscope 80, in which a linear drive 84 is implemented for adjustment of the viewing angle φ. The endoscope has a distal shaft 81 as well as a proximal ocular 83. Optionally, connections 82 for light input or for input of fluids and gases may be provided. The endoscope has an axis 88, which preferably is also the optical and/or mechanical axis. At the distal end of the shaft 81, a prism 85 is arranged pivotably around the bearing 86. The prism allows a deflection of the optical beam path, such that light entering into the distal end of the endoscope under various viewing angles φ can be detected. Adjustment of the prism is conducted by means of a linear drive 84 via a push/pull-rod 87.

It will be appreciated to those skilled in the art having the benefit of this disclosure that this invention is believed to provide a linear drive or linear motor and an endoscope. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

LIST OF REFERENCE NUMERALS

10 stator
11 magnetic member
12 first stator pole shoe
13 second stator pole shoe
14 coil
15 first field sensor
16 second field sensor
17 first integrated field sensor
18 second integrated field sensor
19 second coil
20 armature
21 first permanent magnet
22 second permanent magnet
23 first armature pole shoe
24 second armature pole shoe
25 third armature pole shoe
30 center axis
41 first magnetic circuit
42 second magnetic circuit
51 first lens
52 second lens
61 signal curve first field sensor
62 signal curve second field sensor
63 difference of signal curves
64 linear approximation
65 signal curve first integrated field sensor
66 signal curve second integrated field sensor
80 endoscope
81 endoscope shaft
82 connection
83 ocular
84 linear drive
85 prism
86 bearing
87 push/pull-rod
88 center axis

What is claimed is:

1. A linear drive comprising:
a ring-shaped stator having a center axis, the stator further comprising:
a magnetic coil,
a first ring-shaped stator pole shoe and a second ring-shaped stator pole shoe, each pole shoe being at one side of the coil,
a magnetic member enclosing the coil in radial direction
a first field sensor in axial direction next to the coil on the side of the first stator pole shoe,
a second field sensor in axial direction next to the coil on the side of the second stator pole shoe,
a hollow armature being moveable in axial direction in the stator, the armature further comprising:
a first ring-shaped permanent magnet and a second ring-shaped permanent magnet, the permanent magnets being polarized axially in opposite directions,
a ring-shaped center armature pole shoe between the two permanent magnets,
a ring-shaped first outer armature pole shoe at a side of the first permanent magnet, said side being opposite to the middle armature pole shoe in axial direction, and
a ring-shaped second outer armature pole shoe at a side of the second permanent magnet, said side being opposite to the middle armature pole shoe in axial direction,
wherein at least a part of the magnetic flux of the first outer armature pole shoe and the second outer armature pole shoe goes through at least one of the field sensors.

2. The linear drive according to claim 1, wherein at least one of the field sensors is arranged in an opening of a respective stator pole shoe, or is integrated in the stator pole shoe or is enclosed by the magnetic member in radial direction.

3. The linear drive according to claim 1, wherein an evaluation circuit is provided, the evaluation circuit generates a signal for indicating the position of the armature by means of the sum of signals of the both field sensors and/or it compares a setpoint value for a position of the armature with a measured value of at least one signal of at least one field sensor, and generates a control signal for keeping the position of the armature constant.

4. The linear drive according to claim 1, wherein at least one stator pole shoe and/or at least one armature pole shoe and/or the magnetic member comprises at least one ferromagnetic material.

5. The linear drive according to claim 1, wherein the armature has a bore for holding an optical element.

6. The linear drive according to claim 1, wherein a sliding sleeve with a non-ferromagnetic material having a low friction coefficient is arranged at a surface between stator and armature.

7. The linear drive comprising:
a ring-shaped stator having a center axis, the stator further comprising:
a magnetic coil, having a ring-shaped stator pole shoe at one side in the direction of the center axis,
a magnetic member enclosing the coil in radial direction,
a field sensor integrated into the stator pole shoe,
a hollow armature being moveable in axial direction in the stator, the armature further comprising:
a ring-shaped permanent magnet,
a ring-shaped first outer armature pole shoe and a ring-shaped second outer armature pole shoe, the pole shoes being at axially opposite sides of the permanent magnet,
wherein at least a part of the magnetic flux of the first outer armature pole shoe goes through the field sensor.

8. The linear drive according to claim 7, further comprising a second field sensor, the second field sensor being integrated in the stator pole shoe and displaced in axial direction against the first field sensor.

9. The linear drive according to claim 7, wherein the field sensor is arranged in an opening of a respective stator pole shoe, or is integrated in the stator pole shoe or is enclosed by the magnetic member in radial direction.

10. The linear drive according to claim 7, wherein an evaluation circuit is provided, the evaluation circuit generates a signal for indicating the position of the armature by means of the sum of signals of the both field sensors and/or it compares a setpoint value for a position of the armature with a measured value of at least one signal of at least one field sensor, and generates a control signal for keeping the position of the armature constant.

11. The linear drive according to claim 7, wherein at least one stator pole shoe and/or at least one armature pole shoe and/or the magnetic member comprises at least one ferromagnetic material.

12. The linear drive according to claim 7, wherein the armature has a bore for holding an optical element.

13. The linear drive according to claim 7, wherein a sliding sleeve with a non-ferromagnetic material having a low friction coefficient is arranged at a surface between stator and armature.

14. The linear drive comprising:
a ring-shaped stator having a center axis, the stator further comprising:
a first magnetic coil and a second magnetic coil,
a ring-shaped stator pole shoe, the stator pole shoe being arranged between the magnetic coils,
a magnetic member enclosing the coils in radial direction
a first field sensor and a second field sensor, both field sensors being integrated in the stator pole shoe and are displaced in axial direction against each other,
a hollow armature being moveable in axial direction in the stator, the armature further comprising:
a first ring-shaped permanent magnet and a second ring-shaped permanent magnet, the permanent magnets polarized axially in opposite directions,
a ring-shaped center armature pole shoe between the two permanent magnets,
a ring-shaped first outer armature pole shoe at a side of the first permanent magnet, said side being opposite to the middle armature pole shoe in axial direction, and
a ring-shaped second outer armature pole shoe at a side of the second permanent magnet, said side being opposite to the middle armature pole shoe in axial direction,
wherein at least a part of the magnetic flux of the center armature pole shoe goes through at least one of the field sensors.

15. The linear drive according to claim 14, wherein at least one of the field sensors is arranged in an opening of a respective stator pole shoe, or is integrated in the stator pole shoe or is enclosed by the magnetic member in radial direction.

16. The linear drive according to claim 14, wherein an evaluation circuit is provided, the evaluation circuit generates a signal for indicating the position of the armature by means of the sum of signals of the both field sensors and/or it compares a setpoint value for a position of the armature with a measured value of at least one signal of at least one field sensor, and generates a control signal for keeping the position of the armature constant.

17. The linear drive according to claim 14, wherein at least one stator pole shoe and/or at least one armature pole shoe and/or the magnetic member comprises at least one ferromagnetic material.

18. The linear drive according to claim 14, wherein the armature has a bore for holding an optical element.

19. The linear drive according to claim 14, wherein a sliding sleeve with a non-ferromagnetic material having a low friction coefficient is arranged at a surface between stator and armature.

20. A camera with a linear drive according to claim 1, wherein the linear drive is provided for the control of at least one optical component.

21. An endoscope with a linear drive according to claim 1, wherein the linear drive is provided for the control of at least one optical component.

22. A medical instrument having a linear drive according to claim 1, wherein the linear drive is provided for adjusting the aperture angle of a jaw section.

23. The camera with a linear drive according to claim 7, wherein the linear drive is provided for the control of at least one optical component.

24. Endoscope with a linear drive according to claim 7, wherein the linear drive is provided for the control of at least one optical component.

25. The medical instrument having a linear drive according to claim 7, wherein the linear drive is provided for adjusting the aperture angle of a jaw section.

* * * * *